United States Patent [19]

Harper et al.

[11] Patent Number: 5,942,211
[45] Date of Patent: *Aug. 24, 1999

[54] ANTISEPTIC DENTIFRICE

[75] Inventors: D. Scott Harper, Glen Rock; Rita M. Parikh, Paramus; Dhananjaya Alli, West Orange; Anil Talwar, Long Valley, all of N.J.

[73] Assignee: Warner-Lambert Company, Morris Plains, N.J.

[ * ] Notice: This patent issued on a continued prosecution application filed under 37 CFR 1.53(d), and is subject to the twenty year patent term provisions of 35 U.S.C. 154(a)(2).

[21] Appl. No.: 08/774,990

[22] Filed: Dec. 27, 1996

Related U.S. Application Data

[63] Continuation of application No. 08/280,098, Jul. 25, 1994, abandoned.

[51] Int. Cl.[6] .............................. A61K 7/16; A61K 7/18; A61K 7/26
[52] U.S. Cl. ................................. 424/49; 424/52; 424/58
[58] Field of Search ........................................ 424/49–58

[56] References Cited

U.S. PATENT DOCUMENTS

| | | |
|---|---|---|
| 1,526,940 | 2/1925 | Staegemann . |
| 3,164,524 | 1/1965 | Fand et al. ................................. 167/93 |
| 3,699,221 | 10/1972 | Schole et al. .............................. 424/54 |
| 3,937,803 | 2/1976 | Delaney et al. ........................... 424/49 |
| 3,988,434 | 10/1976 | Schole et al. .............................. 424/54 |
| 4,272,513 | 6/1981 | Gaffar ....................................... 424/52 |
| 4,550,018 | 10/1985 | Ambike et al. ............................ 424/52 |
| 4,812,306 | 3/1989 | Cocherell et al. ......................... 424/52 |
| 4,830,221 | 5/1989 | Mazzanobile ............................. 222/92 |
| 4,945,087 | 7/1990 | Tazwar et al. ............................. 514/60 |
| 4,950,479 | 8/1990 | Hill et al. .................................. 424/49 |
| 5,004,596 | 4/1991 | Cocerell et al. ........................... 424/52 |
| 5,094,843 | 3/1992 | Mazzanobile et al. .................... 424/52 |
| 5,149,521 | 9/1992 | Hirose et al. .............................. 424/58 |
| 5,186,926 | 2/1993 | Williams et al. .......................... 424/53 |
| 5,275,803 | 1/1994 | Dawson .................................... 424/52 |
| 5,279,814 | 1/1994 | Wuelknitz et al. ........................ 424/52 |
| 5,281,412 | 1/1994 | Lukacovic et al. ........................ 424/52 |
| 5,286,496 | 2/1994 | Stapler et al. ........................... 424/490 |
| 5,288,480 | 2/1994 | Gaffar et al. .............................. 424/52 |
| 5,292,500 | 3/1994 | Wuelknitz et al. ........................ 424/49 |
| 5,292,526 | 3/1994 | Gaffer et al. .............................. 424/49 |
| 5,292,528 | 3/1994 | Mori et al. ................................. 424/54 |
| 5,298,238 | 3/1994 | Hussein et al. ............................ 424/49 |
| 5,356,615 | 10/1994 | Saffar ....................................... 424/49 |

FOREIGN PATENT DOCUMENTS

| | | |
|---|---|---|
| 834131 | 2/1970 | Canada . |
| 0528457 | 7/1992 | European Pat. Off. ......... A61K 7/16 |
| 497476 | 8/1992 | European Pat. Off. . |
| 0579333 | 7/1993 | European Pat. Off. ......... A61K 7/16 |
| 2445676 | 9/1974 | Germany ......................... A61K 7/26 |
| 208481 | 1/1990 | Hungary .......................... A61K 7/16 |
| 59-175410 | 3/1983 | Japan .............................. A61K 7/16 |
| 06016526 | 1/1994 | Japan .............................. A61K 31/20 |
| 337129 | 5/1972 | Russian Federation ......... A61K 7/16 |
| 1161018 | 11/1967 | United Kingdom ............. A61K 7/16 |
| 9204884 | 4/1992 | WIPO . |
| 9416674 | 8/1994 | WIPO . |

OTHER PUBLICATIONS

Mandel, I.D.: Chemotherapeutic agents for controlling plaque and gingivitis. J Clin Periodontol. 1988; 15:488–498.
Guenther, E.: Esters. The Essential Oils: vol. II, The Constituents of Essentials, 1949; pp.224–225, 500–502, 640–641, 708–710.
Chilson, F.: Modern Cosmetics, 2nd ed, 1938; pp. 183–184.
Meeker et al: The antibactrial action of eugenol, thyme oil, and related essential oils used in dentistry. Conpend Cont. Ed. Dent., vol. IX, No. 1, Article 3, pp. 36–41.
Janistyn, H.: Taschenbuch Der Modernen Parfumerie und Kosmetik, 1966; pp. 535–536.
"Euthymol" Reg. U.S. Trademark 58085 Dec. 4, 1906 Dentifrices Toilet Creams Toilet Powders.
"Listerine" Reg. U.S. Trademarks 41,413 45682 55690 57563 85150 117884168 221121 (240162—Toothpaste—"Since 1881") 239895 240162 244676 834258 923970.
Listerine Toothpaste Advertisements (Lambert Pharmacal Co) Jul. 1932, Mar. 1935, Mar. 1936.
Original Euthymol Toothpaste Carton & Labels (Warner Lambert Healthcare Division of Warner Lambert Group.
Listerine Antiseptic Label Copyright 1991 Warner Lambert Co. ADA Seal of Approval (Ingredients Listed On Label).
Approval of Listerine: The Background Biological Therapies In Dentistry 3(11) Apr. 1988 (2pp.).
Bennett et al Journal Of Consumer Affairs 27(2): 397–416 Winter 1993 Public Policy Issues in the Marketing of Seals of Approval.
Consumer Reports 54:504–510 Aug. 1989 "New Ways to Save Your Teeth?".
Listerine Toothpaste—Cool Mint Jul. 11, 1994 Product Alert 24(28) Market Intelligence Service, Ltd. "Warner–Lambert Co. Plans to Test Market Listerine Cool Mint Toothpaste in Canada".
A.Ph.A. Handbook of non Prescription Drugs 8th ED( ) p. 946 Toothpaste Product Table Listerine Toothpaste.
Listerine Antiseptic ADA Accepted American Dental Association.
Winters Advertising Age 59(20): 40 May 9, 1988 Listerine Goes On Offensive (Abstract).
Mahler Wall Street Journal 224(16)Jul. 25, 1994 Gronddaddy Listerine Bottle is Antigent (Abstract).
Adweek 33(13) Mar. 30, 1992 p. 32 Cool Mint Listerine No More Medicine Breath (Abstract).
Sears America Health 8(3): 50 Apr. 1989 FDA To Review Aniplaque Claims (Abstract).
Adweek's Marketing Week 29(48) 26, 30 Oct. 31, 1988 Plaque Fighters (Abstract).
Freeman Advertising Age 58(8) 24 Feb. 23, 1987 Oral Vises On Rese (Abstract).
Weicz Broadweek 35(29):1,6 Jul. 18, 1994 Betting the Mint (Abstract).

*Primary Examiner*—Shep K. Rose
*Attorney, Agent, or Firm*—Jean B Barish; Evan J. Federman

[57] ABSTRACT

An improved stable acidic antiseptic dentifrice composition with therapeutically effective amounts of essential oils formulated at a pH of between 3.0 and 5.5 is disclosed. Also disclosed is an improved stable acidic antiseptic and anticaries dentifrice composition with essential oils and one or more fluorine-releasing compounds, formulated at a pH of between 3.0 and 5.5.

17 Claims, No Drawings

ANTISEPTIC DENTIFRICE

This is a continuation application of U.S. Ser. No.: 08/280,098, filed on Jul. 25, 1994 now abandoned.

FIELD OF THE INVENTION

The present invention is related to an antiseptic dentifrice composition to help reduce oral malodor and caries, containing essential oils and formulated to a pH of between about 3.0 and about 5.5.

BACKGROUND OF THE INVENTION

Volatile or essential oils are widely used in oral care products. Essential oils are aromatic compounds that are either derived from plant sources or are synthesized. Some essential oils show long-lasting germicidal effectiveness against the most common pathogens in the mouth. These pathogens are frequently associated with oral malodor, plaque, and gingivitis. Thymol is an essential oil that is well-known and widely used as an antimicrobial in oral care products. Other essential oils include menthol, methyl salicylate, eucalyptol, anethol and eugenol.

Essential oils have been used for years in antiseptic and antiplaque mouthwash solutions. For example, LISTERINE® antiseptic mouthwash has been marketed since 1881, and contains the essential oils thymol, menthol, eucalyptol, and methyl salicylate. More recently, essential oils have been included in formulations of toothpaste. U.S. Pat. No. 1,526,940 to Staegemann teaches a toothpaste with the germicide ammonium ichthyol sulphonate with high amounts of thymol, menthol, eucalyptol, methyl salicylate, and peppermint oil as flavorants and taste-masking ingredients.

U.S. Pat. No. 3,164,524 to Fand et al. teaches an oral antiseptic comprising 2, 2'-thiobis-(4,6-dichlorophenol), boric acid, methyl salicylate, thymol, menthol and eucalyptol.

U.S. Pat. No. 5,094,843 to Mazzanobile et al. teaches an anti-plaque, anti-gingivitis toothpaste with a flourine source, and a specific range of thymol, menthol, methyl salicylate and eucalyptol.

European Patent Application 04974776 to Colgate-Palmolive Co. teaches an antiplaque oral composition, including a toothpaste, with triclosan. The antiplaque activity of the triclosan is increased by essential oils such as eucalyptol, thymol, methyl salicylate, and menthol.

U.S. Patents Nos. 4,545,979 and 4,550,018 to Ambike et al. teach a dental hygiene composition in an acidic pH range of from 3.0 to 5.0, pH buffers, fluoride, thymol, eucalyptol, methyl salicylate, peppermint and spearmint oil flavors, and 0.1 to 2.0 percent by weight of one or more highly pure alkali metal salts of dodecyl sulphate having less than 5% non-dodecyl alkyl sulphate salts.

Canadian Pat. No. 834131 to Tisserand teaches a dentifrice preparation that has an acidic pH of about 3.8 to 5.8, optimally a pH of 4.0 to 5.5, and most preferably a pH of 4.0 to 4.8; fluoride; and menthol, methyl salicylate and thyme oil flavor oils that are substantially free of hydrocarbon terpenes. According to Tisserand when essential oils which are not free of terpenes are employed in a fluoride dentifrice which has a pH in the range of about 3.8 to 5.8 the flavor develops a pronounced rancid and sour taste in a period of less than 3 months.

Warner-Lambert has marketed Euthymol® Toothpaste that was formulated with thymol, eucalyptol, methyl salicylate and menthol at a pH above 7.0. This toothpaste was not formulated with fluoride. Warner-Lambert has also marketed Listerine® toothpaste in the United States and Canada that did not contain thyrmol or eucalyptol and was formulated at a pH above 6.0. This toothpaste did not contain fluoride.

Mazzanobile et. al, U.S. Pat. No. 4,830,221 discloses a dentifrice formulated at a pH of between about 3.5 and about 9.5. Eucalyptus, thyme, menthol, and methyl salicylate are among the flavoring oils that are disclosed. There is no mention of the use of flavor oils in antiseptically effective amounts.

While the prior art discloses toothpaste and other dentifrice compositions with antiseptic essential oils, there is no teaching or suggestion regarding the optimum pH at which these compositions containing essential oils should be formulated. It has surprisingly been found that the antiseptic activity of dentifrice compositions with essential oils is enhanced when the pH of the composition is between about 3.0 and about 5.5.

It is therefore an object of the present invention to provide an antiseptic dentifrice composition that helps reduce oral malodor, formulated with essential oils at an acid pH of between about 3.0 and about 5.5 to enhance the antiseptic activity of the composition.

Another object of this present invention is to provide an antiseptic and anticaries dentifrice composition with essential oils and a fluoride-releasing compound formulated at an acid pH of between about 3.0 and 5.5 to enhance the antiseptic activity of the composition while maintaining effective anticaries activity.

SUMMARY OF THE INVENTION

The present invention is directed to an improved stable acidic antiseptic dentifrice composition comprising the essential oil thymol and/or other essential oils and combinations thereof. The dentifrice composition has an acid pH of about 3.0 to about 5.5. In this pH range the antiseptic activity of the dentifrice composition is enhanced.

The present invention is further directed to an improved stable acidic antiseptic and anticaries dentifrice composition comprising the essential oil thymol and/or other essential oils, and combinations thereof, and one or more fluoride-releasing compound. This dentifrice composition has an acid pH of about 3.0 to about 5.5.

One preferred embodiment comprises an improved stable acidic antiseptic and anticaries dentifrice composition with optimally adjusted concentrations of essential oils and one or more fluoride-releasing compound, combined with abrasives, gelling systems, ancillary flavor systems, and other additives formulated to have acceptable cosmetic properties at a pH of about 3.0 to about 5.5.

DETAILED DESCRIPTION OF THE INVENTION

A dentifrice composition is defined as a composition that is to be used in conjunction with a toothbrush to clean the accessible tooth surfaces. Dentifrice compositions of this invention contain essential oils that have antiseptic properties. Another embodiment of this invention contains essential oils and one or more fluoride-releasing compound. This embodiment has antiseptic and anticaries activity. Dentifrice compositions of this invention also contain, but are not limited to, one or more of the following dentifrice additives: acidifiers, abrasives, surfactants, binders and thickeners, humectants, sweeteners, desensitizing agents, flavors, colors, and preservatives. The dentifrice composition of the invention is acidified to a pH of about 3.0 to about 5.5 by acidifiers including, but not limited to, phosphoric acid, acidic phosphate salts, benzoic acid, and food grade acids (e.g. citric acid). The preceding active ingredients and additives are combined in a hydrous or anhydrous vehicle to form a solid (i.e. toothpowder), a semi-solid (i.e. paste or gel), or a liquid.

Essential oils are volatile aromatic oils which may be synthetic or may be derived from plants by distillation, expression or extraction, and which usually carry the odor or flavor of the plant from which they are obtained. In the dentifrice composition of this invention, antiseptic activity is provided by essential oils. Some of these essential oils also act as flavoring agents. The essential oils of this invention include but are not limited to thymol, menthol, methyl salicylate (wintergreen oil), eucalyptol, carvacrol, camphor, anethole, carvone, eugenol, isoeugenol, limonene, osimen, n-decyl alcohol, citronel, a-salpineol, methyl acetate, citronellyl acetate, methyl eugenol, cineol, linalool, ethyl linalaol, safrola vanillin, spearmint oil, peppermint oil, lemon oil, orange oil, sage oil, rosemary oil, cinnamon oil, pimento oil, laurel oil, cedarleaf oil, and clove oil. Essential oils may be in the dentifrice composition of the present invention in an amount of from about 0.1% w/w to about 4.0% w/w; preferably in an amount of from about 0.5% w/w to about 3.0% w/w; and most preferably in an amount of from about 1.0% w/w to about 2.0% w/w.

Thymol, also known by the chemical formula 5-methyl 2-(1-methylethyl) phenol, is obtained from the essential oil of *Thymus vulgaris Labiatae* and *Monarda punctata Labiatae*. Thymol is a white crystalline powder with an aromatic odor and taste and is soluble in organic solvents but only slightly soluble in deionized water. Thymol may be in the dentifrice composition of this invention in an amount of from about 0.01% w/w to about 1.0% w/w; preferably in an amount of from about 0.1% w/w to about 0.6% w/w; and most preferably in an amount of from about 0.2% w/w to about 0.5% w/w.

Menthol is isolated principally from the oil of *Mentha arvensis*. In its commercial form, menthol is available as L-menthol crystals obtained from a process involving cooling of the oil. Fractional distillation of peppermint oil which usually contains from about 40% to about 65% menthol represents another important source of menthol. Synthetic sources of L-menthol are also available. Menthol may be in the dentifrice composition of the present invention in an amount of from about 0.01% w/w to about 1.0% w/w; preferably in an amount of from about 0.10% w/w to about 0.7% w/w; and most preferably in an amount of from about 0.1% w/w to about 0.6% w/w.

Eucalyptol, another essential oil with antiseptic properties, is derived from the eucalyptus tree. Having a camphoraceous odor and cooling taste, this essential oil is often combined with other essential oils such as menthol in confection formulations to impart medicinal effect. Combinations of menthol and eucalyptol are widely used. Particularly preferred uses of the menthol-eucalyptol combination include, according to the present invention, dentifrices such as toothpastes or dental gels. Eucalyptol may be in the dentifrice composition of the present invention in an amount of from about 0.01% w/w to about 1.0% w/w; preferably in an amount of from 0.05% w/w to about 0.5% w/w; and most preferably in an amount of from about 0.07% w/w to about 0.4% w/w.

Methyl salicylate is the main ingredient in many essential oils, constituting about 99% of oil of wintergreen (*Gaultheria procumbens*) and sweet birch (*Betula lenta*). Methyl salicylate, which has a distinctive refreshing aroma, is used widely in mouthwashes, chewing gums and other oral and pharmaceutical preparations. Methyl salicylate may be in the dentifrice composition of the present invention in an amount of from about 0.01% w/w to about 1.0% w/w; preferably in an amount of from about 0.04% w/w to about 0.6% w/w; and most preferably in an amount of from about 0.1% w/w to about 0.6% w/w.

The dentifrice composition of the invention may contain the following essential oils in percentages by weight: (a) thymol from about 0.01% w/w to about 1.0% w/w; (b) menthol from about 0.01% w/w to about 1.0% w/w; (c) eucalyptol from about 0.01% w/w to about 1.0% w/w; and (d) methyl salicylate from about 0.01% w/w to about 1.0% w/w.

In the preferred embodiment of the dentifrice composition of the present invention, the dentifrice composition may contain the following essential oils in percentages by weight: (a) thymol from about 0.1% w/w to about 0.6% w/w; (b) menthol from about 0.1% w/w to about 0.7% w/w; (c) eucalyptol from about 0.05% w/w to about 0.5% w/w; and (d) methyl salicylate from about 0.04% w/w to about 0.6% w/w.

In the most preferred embodiment of the dentifrice composition of the present invention, the dentifrice composition may contain the following essential oils in percentages by weight: (a) thymol from about 0.2% w/w to about 0.5% w/w; (b) menthol from about 0.1% w/w to about 0.6% w/w; (c) eucalyptol from about 0.07% w/w to about 0.4% w/w; and (d) methyl salicylate from about 0.1% w/w to about 0.6% w/w.

Fluoride-releasing compounds may be used in this invention and may be fully or slightly water soluble, and are characterized by their ability to release fluoride ions or fluoride-containing ions in water and by their lack of reaction with other components in the composition. In the dentifrice composition of this present invention, anticaries activity is provided by fluoride-releasing compounds. Typical fluoride-releasing compounds are inorganic fluoride salts such as water-soluble alkaline earth metal, alkali metal, and heavy metal salts. Sodium monofluorophosphate, sodium fluoride, stannous fluoride and mixtures thereof are preferred.

The amount of fluoride-releasing compound present in a preferred embodiment of this invention depends upon the type of fluoride-releasing compound employed, the solubility of the fluoride-releasing compound, and the formulation of the dentifrice composition. The fluoride-releasing compound used must be used in a nontoxic amount. In general, the fluoride-releasing compound, when used, will be present in an amount by weight of up to about 1.2% w/w, preferably from about 0.1% w/w to about 1.0% w/w, and most preferably from about 0.175% w/w to about 0.8% w/w, of the dentifrice composition so as to release 800–1500 ppm $F^-$.

The most preferred fluoride-releasing compound in the dentifrice composition of the invention is sodium monofluorophosphate at a concentration from about 0.5% w/w to about 1.0% w/w, more preferably about 0.65% w/w to about 0.88% w/w, or most preferably, 0.76% w/w.

The pH for the preferred embodiment according to the present invention is from about 3.0 to about 5.5. A pH greater than about 5.5 has been found to decrease the antiseptic activity of the dentifrice composition. A pH below about 3.0 is generally found to irritate the oral cavity.

The pH of the claimed dentifrice is adjusted to below 5.5 using suitable food or pharmaceutical grade acidifiers. These could include, but are not limited to, one or a combination of the following: phosphoric acid, benzoic acid, citric acid, or other tricarboxylic acids, and the like. The most preferred acidifiers in the present invention include a mixture of phosphoric acid from about 0.01% w/w to about 3.0% w/w, preferably in the range of from about 0.1% w/w to about 1.5% w/w, and most preferably in the range of from about 0.2% w/w to about 0.75% w/w; monobasic sodium phosphate from about 0.01% w/w to about 1% w/w, preferably from about 0.1% w/w to about 0.5% w/w, and most preferably from about 0.2% w/w to about 0.4% w/w; dibasic sodium phosphate from about 0.001% w/w to about 1.0% w/w, preferably from about 0.01% w/w to about 0.5% w/w, and most preferably from about 0.01% w/w to about 0.05% w/w; and benzoic acid in the range of from about 0.01% w/w to about 1.0% w/w, preferably from about 0.05% w/w to about 0.5% w/w, and most preferably from about 0.08% w/w to about 0.35% w/w. The exact amount of acidifier added will depend on the final pH and buffer capacity desired.

The pH of the products may be buffered with salts of the acids in question. Common buffer systems include phosphoric acid and sodium phosphate salts, or citric acid and sodium citrate. Suitable buffers for use in this invention include citric acid-sodium citrate, phosphoric acid-sodium phosphate, sodium monobasic phosphate-sodium dibasic phosphate, acetic acid-sodium acetate, and benzoic acid and benzoate in amounts up to about 1% w/w, preferably from about 0.05% w/w to about 0.75% w/w of the composition, and most preferably from about 0.1% w/w to about 0.5% w/w of the composition.

The preferred embodiment of the present invention may also contain conventional dentifrice additives including but not limited to humectants, binders, thickeners, surfactants, preservatives, sweeteners, flavors, colors, glycerin, and a buffer. These additives are present in amounts that do not interfere with the antiseptic and anticaries properties of the composition of the present invention.

Surfactants or surface active agents are organic compounds which reduce surface tension between liquids and aid in the dispersion of a composition throughout the oral cavity. The surfactant in the present invention may be anionic, nonionic, or amphoteric. The oral hygiene or dentifrice compositions of the present invention may contain surfactants in amounts up to about 5.0% w/w; preferably from about 0.1% w/w to about 3.0% w/w of the dentifrice composition; and most preferably from about 0.2% w/w to about 2.0% w/w of the dentifrice composition.

The most preferred surfactants are anionic. These anionic surfactants include but are not limited to sodium lauryl sulfate, sodium lauroyl sarcosinate, sodium methyl cocoyl taurate, and disodium lauryl sulfosuccinate.

In the most preferred embodiment the surfactant is the anionic surfactant sodium lauryl sulfate.

Amphoteric surfactants have the capacity to behave as either an acid or a base and include quaternized imidazole derivatives useful in the present invention. Preferred amphoteric surfactants include long chain (alkyl) amino-alkylene aklylated amine derivatives, also known as MIRANOL®, manufactured by Rhone-Poulanc, Cranberry, N.J.

Sweeteners well known in the art, including natural and artificial sweeteners, may be used. The sweetener may be selected from a wide range of materials including naturally occurring water-soluble sweeteners, artificial water-soluble sweeteners and modified water-soluble sweeteners derived from naturally occurring water-soluble sweeteners. Artificial water-soluble sweeteners include, but are not limited to, soluble saccharin salts, e.g., sodium or calcium saccharin salts, cyclamate salts, the sodium, ammonium or calcium salt of 3,4-dihydro-6-methyl-1,2,3-oxathiazine-4-one-2,2-dioxide, the potassium salt of 3,4-dihydro-6-methyl-1,2,3-oxathiazine-4-one-2,2-dioxide (Acesulfame-K), the free acid form of saccharin, and the like; dipeptide based sweeteners, such as L-aspartic acid derived sweeteners, e.g., L-aspartyl-L-phenylalanine methyl ester (Aspartame) and materials described in U.S. Pat. No. 3,492,131, L-alpha-aspartyl-N-(2,2,4,4-tetramethyl-3-thietanyl)-D-alaninamide hydrate (Alitame), methyl esters of L-aspartyl-L-phenylglycerine, and L-aspartyl-L-2,5-dihydrophenylglycine, L-aspartyl-2,5-dihydro-L-phenylalanine; L-aspartyl-L-(1-cyclohexene)-alanine, and the like. Naturally occurring water-soluble sweeteners include, but are not limited to, sugar alcohols, including sorbitol as 70% sorbitol solution, mannitol, xylitol, maltitol, hydrogenated starch hydrolysates and mixtures thereof.

Water-soluble sweeteners derived from naturally occurring water-soluble sweeteners include, but are not limited to, chlorinated derivatives of sucrose, known, for example, under the product designation of Sucralose; and protein-based sweeteners such as thaumaoccous danielli (Thaumatin I and II).

Sorbitol solution supplies sweetness and body to the composition and gives a desirable mouth feel. Sorbitol solution also enhances flavor, prevents harsh taste and provides a fresh and lively sensation in the mouth. It also prevents caking of the dentifrice.

In general, an effective amount of sweetener is utilized to provide the level of sweetness desired in any particular embodiment of the dentifrice compositions according to the present invention. This amount will vary with the sweetener selected and the final oral hygiene product. The amount of sweetener normally present is from about 0.0025% w/w to about 60% w/w of the dentifrice composition. The exact range of amounts for each type of sweetener in a dentifrice is well known in the art and is not the subject of the present invention.

The flavors which may be used in the invention include natural and artificial flavors known in the dentifrice art. Suitable flavors include, but are not limited to, mints, such as peppermint, citrus flavors such as orange and lemon, artificial vanilla, cinnamon, various fruit flavors, and the like. Anethole (or anise camphor, p-propenyl anisole) is a flavor constituent of anise and fennel oils which are used widely as flavoring agent and antiseptic and was found useful in masking the harsh taste of thymol.

The amount of flavor is normally a matter of preference subject to such factors as the type of final dentifrice composition, the individual flavor employed, and the strength of flavor desired. The flavors are preferably utilized in amounts that may range in total amounts from about 0.01% w/w to about 6% w/w of the dentifrice composition.

Coloring agents in this invention are used in amounts effective to produce a dentifrice of the desired color. These coloring agents may be incorporated in amounts up to about 3% by weight of the dentifrice composition of the present invention. The coloring agents may also include natural food colors and dyes suitable for food, drug and cosmetic applications. These coloring agents are known as FD & C dyes and lakes. The materials acceptable for the foregoing uses are preferably water-soluble. Illustrative nonlimiting examples include the indigoid dye known as FD & C Blue No. 1, and D & C Yellow No. 10. A full recitation of all FD & C colorants and their corresponding chemical structures may be found in the Kirk-Othmer Encyclopedia of Chemical Technology, 3rd Edition, in volume 5 at pages 857–884. A preferred opacifier, titanium dioxide, may be incorporated in amounts up to about 2.0% w/w, preferably less than about 1.0% w/w of the composition, and most preferably less than about 0.4% w/w.

Suitable humectants in this invention include sorbitol, as 70% sorbitol solution, glycerin, propylene glycol, polyethylene glycol, mixtures thereof, and the like. Humectants may be present in amounts from about 1.0% to about 75.0% by weight of the dentifrice composition.

Suitable abrasive substances for use in this invention include hydrated silica, calcium carbonate, calcium pyrophosphate, dicalcium phosphate dihydrate, or alkali metal meta-phosphates. Silica abrasives in the dentifrice composition according to this invention may include among others, ZEODENT® (113), manufactured by J. M. Huber Corp. and SYLOIDO or SYLODENT®, manufactured by W. R. Grace Co. These polishing agents may be used in amounts up to about 75.0% w/w of the composition, preferably in amounts from about 5.0% w/w to about 40% w/w of the composition, and most preferably from about 5.0% w/w to about 30.0% w/w of the composition.

In the preferred embodiment of this invention, the dentifrice composition includes an oral vehicle and is in the form of toothpaste or a dental gel.

The dentifrice composition of this invention may also include binders or gelling agents to give the products their characteristic consistency. Gelling agents such as hydroxyethyl cellulose, carboxymethyl cellulose, methyl cellulose, xanthan gum, gelling silicas, and the like may be used singly or in combination. The preferred gelling system is a mixture of carboxy methyl cellulose, xanthan gum and gelling silica. Gelling agents may be used in amounts from about 0.5% w/w to about 30% w/w, preferably from about 5.0% w/w to about 15.0% w/w of the dentifrice composition, and most preferably from about 7.0% w/w to about 20% w/w of the composition.

The dentifrice composition of this invention may also contain a desensitizing agent such as strontium chloride, potassium nitrate or sodium citrate-citric acid, which may be used in an amount from about 0.5% w/w to about 10% w/w.

Suitable preservatives in this invention include benzoic acid, butylated hydroxyanisole (BHA), butylated hydroxytoluene (BHT), ascorbic acid, methyl paraben, propyl paraben, tocopherols and mixtures thereof. Preservatives when used are generally present in amounts up to about 1.0% w/w, and preferably from about 0.1% w/w to about 1.0% w/w of the dental gel composition.

The present invention extends to methods of making the improved oral antiseptic compositions. In such a method, an oral antiseptic dentifrice composition according to the present invention is made by first combining water, part of the humectant, one or more sweeteners, phosphate salts and benzoic acid. If fluoride-releasing compounds are used, they are added in this step. The remainder of the humectant is separately combined with one or more gums, and then combined with the first mixture. Titanium dioxide and silicas are separately mixed, and combined with the other mixture previously prepared. Finally, colors, flavors, and surfactants are added and mixed. The pH is adjusted, as needed, with acidifiers. A vacuum is pulled if necessary for deaeration. The pH of a 25.0% w/w aqueous solution of the composition is measured using a suitable pH meter (e.g. Orion Research Microprocessor pH/millivolt Meter, Model 811).

The apparatus useful in accordance with the present invention comprises mixing apparatus well known in the dental art, and therefore the selection of the specific apparatus will be apparent to the artisan.

The present invention is further illustrated by the following examples which are, however, not included to limit the effective scope of the claims. All parts and percentages in the examples and throughout the specification and claims are by weight of the final composition unless otherwise specified.

EXAMPLES

Assay for Dentifrice Antiseptic Activity

The relative antiseptic activity of the dentifrice compositions of the invention and other dentifrice compositions was tested using a kinetic kill time assay of bacterial suspensions, in particular *Pseudomonas aeruginosa* ATCC strain 10145 as the preferred test organism. According to this assay, bacterial suspensions containing approximately $10^8$–$10^9$ organisms per ml were vigorously mixed with 25% slurries of dentifrice (1 part dentifrice: 3 parts diluent, w/v as described below) in a 1:9 ratio. Ten µL aliquots of the assay mixture were removed with sterile bacteriological loops and streaked on nutrient agar at 30, 60, and 120 seconds, which periods are presumed to represent the range of time typically spent in toothbrushing. In Experimental Example 1 water was used as the dentifrice diluent. In Experimental Examples 2 & 3, 0.05 M phosphate buffered saline was used as a diluent. Relative antiseptic activity of the dentifrice was rated as a function of the number of surviving organisms remaining over time. When there were fewer than 100–150 colonies, actual counts were made; denser growth was estimated in three categories, based on a certain colony density, as e.g., 150–300, 300–700, and confluent.

Experimental Example 1

Dentifrice formulations of this invention were prepared using ingredients and quantities as shown in Table 1. Comparative Formula A was made according to the example in the specification of U.S. Pat. No. 5,094,843 to Mazzanobile et al. Comparative Formula B was identical to Comparative Formula A except that Comparative Formula B was acidified to a pH of 4.5 with phosphoric acid. Formulas 1.1–1.3 of this invention were formulated with increasing levels of the essential oils thymol, menthol, methyl salicylate and eucalyptol. Formula 1.4 of this invention contained only thymol, at the concentration contained in Formula 1.3. Formulas 1.1–1.4 of this invent ion all had pH levels of approximately 4.5±0.05. All amounts are expressed in percent by weight of the total composition.

Table 2 shows results from antiseptic activity assays run on the formulations in Table 1. The data demonstrate the following:

Comparative Formula A had a pH of 6.67, and exhibited no detectable antiseptic activity. Comparative Formula B, identical to Comparative Formula A except that it had been acidified to a pH of 4.5, showed markedly increased antiseptic activity compared to Comparative Formula A. These data clearly show the critical effect that pH has on antiseptic activity of dentifrice compositions containing essential oils. The antiseptic activity of Comparative Formula B was not as high as that of Inventive Formulas 1.1–1.4. Since the level of essential oils in Comparative Formula B and Inventive Formula 1.1 are similar, the improved antiseptic activity of Inventive Formula 1.1 suggests that other ingredients in Inventive Formula 1.1 optimized the antiseptic activity of the essential oils. The high level of antiseptic activity of Formulas 1.1–1.4 indicates that this activity occurs over a range of essential oil concentrations and combinations, providing that the pH of the composition is maintained at about 4.5.

TABLE 1

Formulations Used in Experimental Example 1

| | FORMULA NUMBER | | | | | |
|---|---|---|---|---|---|---|
| | A | B | 1.1 | 1.2 | 1.3 | 1.4 |
| PH | 6.67 | 4.5 | 4.46 | 4.46 | 4.51 | 4.51 |
| THYMOL | 0.291 | 0.291 | 0.310 | 0.479 | 0.639 | 0.479 |
| METHYL SALICYLATE | 0.324 | 0.324 | 0.300 | 0.450 | 0.600 | 0 |
| MENTHOL | 0.226 | 0.226 | 0.210 | 0.318 | 0.425 | 0 |
| EUCALYPTOL | 0.389 | 0.389 | 0.460 | 0.691 | 0.922 | 0 |
| GLYCERINE | 10.000 | 10.000 | 6.000 | 6.000 | 6.000 | 6.000 |
| SORBITOL SOLUTION (70%) | 36.640 | 36.640 | 32.000 | 32.000 | 32.000 | 32.000 |
| WATER | 21.339 | 19.839 | 36.580 | 35.922 | 35.274 | 36.423 |
| PEG 400 | 3.000 | 3.000 | 0 | 0 | 0 | 0 |
| PROPYLENE GLYCOL | 0 | 0 | 0 | 0 | 0 | 0.958 |
| XANTHAN GUM | 0.900 | 0.900 | 1.000 | 1.000 | 1.000 | 1.000 |
| Na CMC 12M31P | 0 | 0 | 0.500 | 0.500 | 0.500 | 0.500 |
| $Na_2PO_3F$ (MFP) | 0 | 0 | 0.760 | 0.760 | 0.760 | 0.760 |
| SODIUM FLUORIDE | 0.221 | 0.221 | 0 | 0 | 0 | 0 |
| Na SACCHARIN | 0.214 | 0.214 | 0.350 | 0.350 | 0.350 | 0.350 |
| $NaH_2PO_4$ (monobasic) | 0 | 0 | 0.250 | 0.250 | 0.250 | 0.250 |
| $Na_2HPO_4$ (dibasic) | 0 | 0 | 0.030 | 0.030 | 0.030 | 0.030 |
| BENZOIC ACID | 0 | 0 | 0.250 | 0.250 | 0.250 | 0.250 |
| SODIUM BENZOATE | 0.200 | 0.200 | 0 | 0 | 0 | 0 |
| $TiO_2$ | 0.956 | 0.956 | 1.000 | 1.000 | 1.000 | 1.000 |
| GELLING SILICA | 10.000 | 10.000 | 6.000 | 6.000 | 6.000 | 6.000 |
| ABRASIVE SILICA | 4.000 | 14.000 | 11.000 | 11.000 | 11.000 | 11.000 |
| PHOSPHORIC ACID (25% Aq.) | 0 | 1.500 | 1.500 | 1.500 | 1.500 | 1.500 |
| SLS | 1.300 | 1.300 | 1.500 | 1.500 | 1.500 | 1.500 |

TABLE 2

Antiseptic Activity of Table 1 Formulas

| | | BACTERIAL RECOVERY* | | |
|---|---|---|---|---|
| FORMULA # | pH | 0.5 MIN | 1 MIN | 2 MIN |
| A | 6.67 | CONFLUENT | CONFLUENT | CONFLUENT |
| B | 4.5 | CONFLUENT | ≈500 | 1 |
| 1.1 | 4.46 | 22 | 0 | 0 |
| 1.2 | 4.46 | 0 | 0 | 0 |
| 1.3 | 4.51 | 0 | 0 | 0 |
| 1.4 | 4.51 | 2 | 1 | 1 |

*Colony-forming units surviving

Experimental Example 2

A split factorial designed study was performed in order to examine the relation between dentifrice pH, abrasive levels, and antiseptic activity of dentifrice compositions using the Inventive Formulations in Table 3. In this study, the pH of the formulations ranged from 3.7 to 5.3. SYLODENT® 750 silica abrasive, available from W. R. Grace Co. was added at levels of 9% and 13% in the compositions formulated at pH 4.4–4.9. Compositions at all other pH levels were formulated with 11% abrasive. The data shown in Table 4 indicates that dentifrice compositions formulated at pH levels of 4.5 or below exhibited similar, high levels of antiseptic activity. The two compositions formulated at pH 4.9 also exhibited significant antiseptic activity, but to a somewhat lesser extent than the products with lower pH. The dentifrice formulated at pH 5.3 indicated significantly less antiseptic activity than the lower pH products. This provides additional evidence of the strong relationship between lower pH and increased antiseptic activity of dentifrices containing essential oils. While the products formulated with 13% silica abrasive demonstrated a trend toward slightly lower levels of antiseptic activity than those formulated with 9% abrasive at the same pH level, the difference is trivial. This indicates that varying abrasive levels between 9% and 13% had no significant impact on antiseptic activity.

TABLE 3

Antiseptic Dentifrice Formulas - pH & Abrasive Variants

| | FORMULA NUMBER | | | | | | |
|---|---|---|---|---|---|---|---|
| | 3.1 | 3.2 | 3.3 | 3.4 | 3.5 | 3.6 | 3.7 |
| pH | 3.7 | 4.09 | 4.12 | 4.5 | 4.9 | 4.9 | 5.29 |
| THYMOL | 0.479 | 0.479 | 0.479 | 0.479 | 0.479 | 0.479 | 0.479 |
| METHYL SALICYLATE | 0.058 | 0.058 | 0.058 | 0.058 | 0.058 | 0.058 | 0.058 |
| MENTHOL | 0.319 | 0.319 | 0.319 | 0.319 | 0.319 | 0.319 | 0.319 |
| EUCALYPTOL | 0.175 | 0.175 | 0.175 | 0.175 | 0.175 | 0.175 | 0.175 |
| PEPPERMINT/ SPEARMINT BLEND | 0.416 | 0.416 | 0.416 | 0.416 | 0.416 | 0.416 | 0.416 |
| GLYCERINE | 6.000 | 6.000 | 6.000 | 6.000 | 6.000 | 6.000 | 6.000 |
| SORBITOL (70%) | 000 | 32.000 | 32.000 | 32.000 | 32.000 | 32.000 | 32.000 |
| WATER, DEIONIZED | 30.713 | 29.663 | 33.613 | 32.613 | 31.263 | 33.923 | 33.863 |

TABLE 3-continued

Antiseptic Dentifrice Formulas - pH & Abrasive Variants

| | FORMULA NUMBER | | | | | | |
|---|---|---|---|---|---|---|---|
| | 3.1 | 3.2 | 3.3 | 3.4 | 3.5 | 3.6 | 3.7 |
| XANTHAN GUM | 1.000 | 1.000 | 1.000 | 1.000 | 1.000 | 1.000 | 1.000 |
| Na CMC 12M31P | 0.400 | 0.400 | 0.400 | 0.400 | 0.400 | 0.400 | 0.400 |
| SODIUM CMC 7MF | 0.400 | 0.400 | 0.400 | 0.400 | 0.400 | 0.400 | 0.400 |
| Na F $PO_4$ (MFP) | 0.760 | 0.760 | 0.760 | 0.760 | 0.760 | 0.760 | 0.760 |
| Na SACCHARIN | 0.800 | 0.800 | 0.800 | 0.800 | 0.800 | 0.800 | 0.800 |
| PHOSPHORIC ACID (25% Aq.) | 3.300 | 2.350 | 2.400 | 1.400 | 0.750 | 2.090 | 0.150 |
| $NaH_2PO_4$ (monobasic) | 0.250 | 0.250 | 0.250 | 0.250 | 0.250 | 0.250 | 0.250 |
| $Na_2HPO_4$ (dibasic) | 0.030 | 0.030 | 0.030 | 0.030 | 0.030 | 0.030 | 0.030 |
| TiO2 | 1.000 | 1.000 | 1.000 | 1.000 | 1.000 | 1.000 | 1.000 |
| GELLING SILICA | 7.000 | 7.000 | 7.000 | 7.000 | 7.000 | 7.000 | 7.000 |
| ABRASIVE SILICA | 11.000 | 13.000 | 9.000 | 11.000 | 13.000 | 9.000 | 11.000 |
| BENZOIC ACID | 0.150 | 0.150 | 0.150 | 0.150 | 0.150 | 0.150 | 0.150 |
| SLS | 1.500 | 1.500 | 1.500 | 1.500 | 1.500 | 1.500 | 1.500 |
| FD&C BLUE 1 (0.1% Aq.) | 2.000 | 2.000 | 2.000 | 2.000 | 2.000 | 2.000 | 2.000 |
| D&C YELLOW 10 (0.1.% Aq.) | 0.250 | 0.250 | 0.250 | 0.250 | 0.250 | 0.250 | 0.250 |

TABLE 4

Antiseptic Activity of Table 3 Formulas

| FORMULA # | pH | BACTERIAL RECOVERY* AFTER EXPOSURE | | |
|---|---|---|---|---|
| | | 0.5 MIN | 1 MIN | 2 MIN |
| 3.1 | 3.7 | 99 | 3 | 2 |
| 3.2 | 4.1 | 22 | 1 | 0 |
| 3.3 | 4.1 | 9 | 1 | 1 |
| 3.4 | 4.5 | 120 | 10 | 8 |
| 3.5 | 4.9 | 144 | 44 | 34 |
| 3.6 | 4.9 | 135 | 38 | 25 |
| 3.7 | 5.3 | >500 | ≈200 | ≈200 |

*Colony forming units (CFU) per time period. Data represent means of duplicate assays conducted on two different days (i.e., N = 4). Confluent growth represents >500 CFU, with a theoretical limit of $10^5$.

Experimental Example 3

Further evidence that the antiseptic activity of the invention derives from the enhanced activity of thymol and other essential oils at low pH is provided by the comparative experiment summarized in Table 5. In this study the antiseptic activities of Inventive Formulas 1.3 and 1.4 were compared to certain commercial dentifrices having pH levels between 6.8 and 4.45. These commercial dentifrices do not contain thymol or antiseptically effective levels of other essential oils. The comparative formulations are formulated at acidic pH ranges to preserve the stability of their fluoride source or other active ingredients. The clear superiority of the Inventive Formulations is evidence of the importance of both antiseptic essential oils and low pH on antiseptic activity.

TABLE 5

Antiseptic Activity of Essential Oil Dentifrices Versus Other Low pH Prior Art Formulations

| FORMULA | pH | BACTERIAL RECOVERY* AFTER EXPOSURE OF | | |
|---|---|---|---|---|
| | | 0.5 MIN | 1 MIN | 2 MIN |
| COMPARATIVE FORMULATION C | 6.8 | CONFLUENT | CONFLUENT | CONFLUENT |
| COMPARATIVE FORMULATION D | 4.5 | CONFLUENT | >500 | ≈250 |
| COMPARATIVE FORMULATION E | 4.45 | CONFLUENT | ≈200 | 0 |
| COMPARATIVE FORMULATION F | 5.36 | CONFLUENT | >500 | >500 |
| COMPARATIVE FORMULATION G | 5.69 | CONFLUENT | >500 | ≈300 |
| COMPARATIVE FORMULATION H | 5.69 | ≈200 | 1 | 0 |
| INVENTIVE FORMULA 1.3 | 4.46 | 1 | 0 | 0 |
| INVENTIVE FORMULA 1.4 | 4.46 | 0 | 0 | 0 |

*Colony forming units per time period. Data represent means of duplicate assays conducted on two different days (i.e., N = 4). Confluent growth represents >500 CFU, with a theoretical limit of $10^5$.

Experimental Example 4

A human oral malodor study was conducted in which a 6 member panel of trained hedonic judges evaluated the breath of 23 human subjects before and up to 4 hours after brushing with Inventive Formulas 1.3 and 1.5, and a placebo control consisting of the unflavored dentifrice base. The study employed a three way crossover design in which each subject brushed with each product, with at least one day between evaluations. The panel of hedonic judges scored the subjects blindly at baseline, and 30, 60, 90, 120, 180 and 240 minutes after brushing using a 9 point scale. The results indicated that brushing with the Inventive Formulas significantly reduced oral malodor scores relative to placebo at all post-brushing evaluations. Inventive Formula 1.5 reduced malodor somewhat better than Inventive Formula 1.3, suggesting a dose response to the antiseptic flavoring system.

Example 5

One kilogram of a preferred embodiment of the invention was prepared with the ingredients shown in Table 6, using mixing and blending techniques described herein above. The pH was adjusted with phosphoric acid to a pH of 4.3 to 4.7. The antiseptic activity of this formulation is comparable to that of Inventive Formulas 1.2–1.4. The dentifrice composition prepared in accordance with the Example exhibited excellent cosmetic properties including acceptable appearance, odor, and taste.

TABLE 6

| Ingredient | Percent W/W |
| --- | --- |
| Glycerin USP Special | 6.000 |
| Xanthan Gum K6B166 | 1.0000 |
| Sodium Carboxymethyl Cellulose Type 12M31 | .6000 |
| Sodium Carboxymethyl Cellulose USP Type | .6000 |
| Water Deionized | 33.0913 |
| Sorbitol Solution USP | 32.0000 |
| Sodium Monofluorophosphate 100% | .7600 |
| Saccharin Sodium (Spray Dried, FCC) | 1.2000 |
| Sodium Phosphate (Monobasic) Anhydrous | .2500 |
| Sodium Phosphate Anhydrous (Dibasic) | .0300 |
| Acid Benzoic USP | .1500 |
| Titanium Dioxide USP | .3500 |
| Hydrated Silicon Dioxide | 7.0000 |
| Silica Amorphous, Synthetic (Sylodent 750) | 11.0000 |
| Sodium Lauryl Sulfate, Washed & Dried | 1.5000 |
| Water Deionized | 2.5000 |
| Thymol NF | .4000 |
| Menthol USP | .1750 |
| Methyl Salicylate NF | .0600 |
| Eucalyptol | .1000 |
| Spearmint Oil Blend, Redistilled | .1000 |
| Peppermint Oil NF/FCC, Crystal White | .2000 |
| Mint Flavor N & A 42603 | .5200 |
| FD and C Blue No. 1 | .0010 |
| D and C Yellow No. 10 | .0001 |
| Phosphoric Acid NF | .4125 |
| Totals | 100.0000 |

What is claimed is:

1. An acidic antiseptic dentifrice composition comprising an antiseptically effective amount of thymol in an amount of from about 0.01% w/w to about 1.0% w/w; menthol in an amount of from about 0.01% w/w to about 1.0% w/w; eucalyptol in an amount of from about 0.01% w/w to about 1.0% w/w; and methyl salicylate in an amount of from about 0.01% w/w to about 1.0% w/w, said composition being buffered to a pH range of from about 3.0 to about 5.5; abrasives that are compatible with a dentifrice composition buffered to a pH range of from about 3.0 to about 5.5; wherein said composition is substantially free from one or more highly pure alkali metal salts of dodecyl sulphate having less than 5% non-dodecyl alkyl sulphate salts; and wherein said composition comprises flavoring oils that are not substantially free of terpenes.

2. The acidic antiseptic dentifrice composition of claim 1 wherein said thymol is in an amount of from about 0.1% w/w to about 0.6% w/w.

3. The acidic antiseptic dentifrice composition of claim 2 wherein said menthol is in an amount of from about 0.1% w/w to about 0.7% w/w.

4. The acidic antiseptic dentifrice composition of claim 3 wherein said methyl salicylate is from about 0.04% w/w to about 0.6% w/w.

5. The acidic antiseptic dentifrice composition of claim 4 wherein said eucalyptol is from about 0.05% w/w to about 0.5% w/w.

6. The acidic antiseptic dentifrice composition of claim 2 wherein said said menthol is about 0.1% w/w to about 0.6% w/w.

7. The acidic antiseptic dentifrice composition of claim 6 wherein said methyl salicylate is about 0.1% w/w to about 0.6% w/w.

8. The acidic antiseptic dentifrice composition of claim 7 wherein said eucalyptol is about 0.07% w/w to about 0.4% w/w.

9. The acidic antiseptic dentifrice composition of claim 8 wherein said thymol is in an amount of from about 0.2% w/w to about 0.5% w/w.

10. The acidic antiseptic dentifrice of claim 1 wherein said abrasives are selected from the group consisting of silica abrasives and alkali metal meta-phosphates.

11. An acidic antiseptic dentifrice composition comprising an antiseptically effective amount of the essential oils thymol, menthol, methyl salicylate and eucalyptol, wherein the total concentration by weight of said essential oils is in an amount of from about 0.1% w/w to about 4.0% w/w, said composition being buffered to a pH range of from about 3.0 to about 5.5; abrasives that are compatible with a dentifrice composition buffered to a pH range of from about 3.0 to about 5.55; wherein said composition is substantially free from one or more highly pure alkali metal salts of dodecyl sulphate having less than 5% non-dodecyl alkyl sulphate salts; and wherein said composition comprises flavoring oils that are not substantially free of terpenes.

12. The acidic antiseptic dentifrice composition of claim 11 wherein the total concentration by weight of said essential oils is an amount of from about 0.5% w/w to about 3.0% w/w.

13. The acidic antiseptic dentifrice composition of claim 12 wherein the total concentration by weight of said essential oils is in an amount of from about 1.0% w/w to about 2.0% w/w.

14. The acidic antiseptic dentifrice composition of claim 1 wherein said composition further comprises at least one flavor oil selected from the group consisting of spearmint oil, cinnamon oil, clove oil, rosemary oil, and peppermint oil.

15. The acidic antiseptic dentifrice of claim 1 further comprising at least one dentifrice additive.

16. A method for preparing the acidic antiseptic dentifrice composition of claim 1 comprising:
   a) admixing water, humectant, sweetener, phosphate salt and benzoic acid to form a first mixture;
   b) admixing a humectant with gum to form a second mixture;
   c) admixing said first and second mixtures to form a third mixture;

d) admixing one or more abrasives that are compatible with a dentifrice composition buffered to a pH range of from about 3.0 to about 5.5, to form a fourth mixture;

e) admixing said third and fourth mixtures to form a fifth mixture;

f) admixing said fifth mixture with an antiseptically effective amount of thymol, menthol, eucalyptol and methyl salicylate, flavors, and surfactant to form a sixth mixture;

g) adjusting the pH of said sixth mixture to a pH of from about 3.5 to about 5.5 with acidifiers;

h) deareating said sixth mixture under a vacuum; wherein said composition is substantially free from one or more highly pure alkali metal salts of dodecyl sulphate having less than 5% non-dodecyl alkyl sulphate salts; and wherein said compositioin comprises flavoring oils that are not substantially free of terpenes.

17. A method of reducing malodor in the human mouth comprising brushing teeth with the dentifrice composition of claim 1.

* * * * *